(12) United States Patent
Wilson et al.

(10) Patent No.: US 7,776,292 B2
(45) Date of Patent: Aug. 17, 2010

(54) METHOD AND APPARATUS FOR BIOWEAPON DECONTAMINATION

(75) Inventors: Deborah E. Wilson, Dunn Loring, VA (US); Katherine K. Lock, Bethesda, MD (US); Murray L. Cohen, Fort Worth, TX (US); Thomas E. McWhorter, Allentown, PA (US); Aaron A. Rosenblatt, New York, NY (US); Theodore J. Traum, Rio Rancho, NM (US)

(73) Assignees: CDIC, Inc., Atlanta, GA (US); The United States of America as represented by the Secretary of the Department of Health and Human Services, Washington, DC (US); CDG Research Corporation, Bethlehem, PA (US)

( * ) Notice: Subject to any disclaimer, the term of this patent is extended or adjusted under 35 U.S.C. 154(b) by 357 days.

(21) Appl. No.: 10/597,191
(22) PCT Filed: Jan. 13, 2005
(86) PCT No.: PCT/US2005/000766
§ 371 (c)(1),
(2), (4) Date: Nov. 7, 2006
(87) PCT Pub. No.: WO2005/123145
PCT Pub. Date: Dec. 29, 2005

(65) Prior Publication Data
US 2008/0139869 A1 Jun. 12, 2008

Related U.S. Application Data
(60) Provisional application No. 60/537,457, filed on Jan. 16, 2004.

(51) Int. Cl.
| | | |
|---|---|---|
| *A61L 2/00* | (2006.01) | |
| *A61L 9/00* | (2006.01) | |
| *A61L 2/20* | (2006.01) | |
| *B01J 19/12* | (2006.01) | |
| *B01D 53/50* | (2006.01) | |
| *B01D 53/68* | (2006.01) | |
| *B01D 21/00* | (2006.01) | |
| *A62D 3/00* | (2007.01) | |
| *C07C 1/00* | (2006.01) | |
| *C07C 2/00* | (2006.01) | |
| *C07C 4/00* | (2006.01) | |
| *C07C 5/00* | (2006.01) | |
| *C07C 6/00* | (2006.01) | |

(52) U.S. Cl. .................. 422/295; 422/22; 422/23; 422/32; 422/33; 422/186.07; 422/292; 422/298; 422/304; 204/157.15; 204/157.43; 210/748; 423/240 R; 588/299

(58) Field of Classification Search ............ 204/157.15, 204/157.43; 210/748; 422/22, 23, 24, 32, 422/33, 34, 186.07, 292, 295, 298, 305; 423/447, 423/240 R; 438/711, 727, 798; 588/299
See application file for complete search history.

(56) References Cited

U.S. PATENT DOCUMENTS
4,298,426 A * 11/1981 Torregrossa et al. ........... 162/57
(Continued)

FOREIGN PATENT DOCUMENTS
| EP | 0 159 660 A2 | 10/1985 |
|---|---|---|
| WO | WO 03/037388 A2 | 5/2003 |
| WO | WO 03/059401 A2 | 7/2003 |

OTHER PUBLICATIONS
Knapp et al., "Chlorine Dioxide as a Gaseous Sterilant," *MD&DI*, Sep. 1986, pp. 48-51.

*Primary Examiner*—Jerry Lorengo
*Assistant Examiner*—Jennifer A Smith
(74) *Attorney, Agent, or Firm*—Klarquist Sparkman, LLP

(57) ABSTRACT

The present disclosure relates to the decontamination of articles contaminated (or thought to be contaminated) with bioweapons, such as methods and apparatus for decontaminating articles contaminated with sporualated bioweapons. In some embodiments, the methods are methods of decontaminating an environment, for example a room or building contaminated with a bioweapon.

33 Claims, 4 Drawing Sheets

U.S. PATENT DOCUMENTS

| | | | |
|---|---|---|---|
| 4,681,739 A * | 7/1987 | Rosenblatt et al. | 422/37 |
| 5,439,654 A * | 8/1995 | Kochte | 422/292 |
| 5,547,590 A * | 8/1996 | Szabo | 210/748 |
| 6,156,267 A * | 12/2000 | Pai et al. | 422/3 |
| 2004/0101438 A1 * | 5/2004 | Nelson et al. | 422/31 |
| 2008/0139869 A1 * | 6/2008 | Wilson et al. | 588/299 |

* cited by examiner

METHOD AND APPARATUS FOR BIOWEAPON DECONTAMINATION

CROSS REFERENCE TO RELATED APPLICATION

This is the U.S. National Stage of International Application No. PCT/US2005/000766, filed Jan. 13, 2005 (published in English under PCT Article 21(2)), which claims the benefit of U.S. Provisional Application No. 60/537,457 filed Jan. 16, 2004, which is hereby incorporated by reference in its entirety.

FIELD

The present disclosure relates to the decontamination of articles that are or may be contaminated with bioweapons, such as sporulated bioweapons, for example anthrax.

BACKGROUND

U.S. mail, postal facilities, and government buildings have in the past been contaminated with weaponized anthrax spores, which resulted in several cases of bioterrorism-related inhalational anthrax infections. Because the U.S. Postal Service currently handles an estimated 239 billion items of mail per year, the risk is high that another disease outbreak will result from acts of bioterrorism. To protect the public health, mail and buildings actually or potentially contaminated with a bioweapon from such an attack must be thoroughly decontaminated.

One problem with the decontamination of bioterrorism sites is that anthrax and other bioweapon spores generally are "weaponized," which changes the spores' native characteristics and makes them more resistant to decontamination. While conventional decontamination protocols, such as exposure to chlorine dioxide, ethylene oxide, formaldehyde, or steam may be sufficient to kill many sporulated bacteria, they often fail to completely inactivate weaponized spores.

Furthermore, even those conventional bioweapon decontamination protocols that are effective on non-porous surfaces typically fail to fully decontaminate porous surfaces, such as paper. For instance, U.S. Pat. No. 4,681,739 discloses a method for decontaminating a bacterial spore-contaminated surface that is substantially gas-impermeable. However, this method is ineffective at decontaminating porous surfaces, particularly porous surfaces that are contaminated with weaponized spores. Reliance on such a method may permit weaponized spores to remain viable and undetected, leading to possible infection and death.

SUMMARY

Provided herein are methods of decontaminating articles that overcomes many of the problems of prior methods. The method is effective at killing weaponized spores, for example when spores are present on a porous or non-pourous article or surface, for which prior approaches are often somewhat ineffective.

In particular examples, the method includes enclosing the article in an environment, humidifying the environment to enhance the susceptibility of the spores to subsequent decontamination with a decontamination gas such as chlorine dioxide, reducing the pressure in the humidified environment to provide a deep vacuum, for example at least as low as 100 inches of water (0.25396 kg/cm$^2$), and then introducing into the environment a concentration of decontamination gas effective to decontaminate the article by killing substantially 100% of the spores. In some examples, the decontamination gas is humidified, for example introduced into the environment with humidification. The disclosed methods are particularly effective at decontaminating porous articles because exposing the article to a deep vacuum has been found to permit effective penetration of the decontamination gas into the porous structure of the object.

In some examples, for example when the environment to be decontaminated is a room or building, the method includes sealing the environment, humidifying the environment to enhance the susceptibility of the spores to subsequent decontamination with a decontamination gas such as chlorine dioxide and then introducing into the environment a concentration of decontamination gas effective to decontaminate the article by killing substantially 100% of the spores. In some examples, the decontamination gas is humidified, for example introduced into the environment with humidification. In examples where the environment to be decontaminated is a room or building, the pressure can be ambient.

Also provided is an apparatus for decontaminating a porous article. The apparatus includes a selectively sealable decontamination chamber, a decontamination chamber humidifier, a source of chlorine dioxide gas in fluid communication with the decontamination chamber, and a decontamination chamber vacuum generator.

The foregoing and other features and advantages will become more apparent from the following detailed description of several embodiments.

DETAILED DESCRIPTION

Abbreviations and Terms

Figure 1:
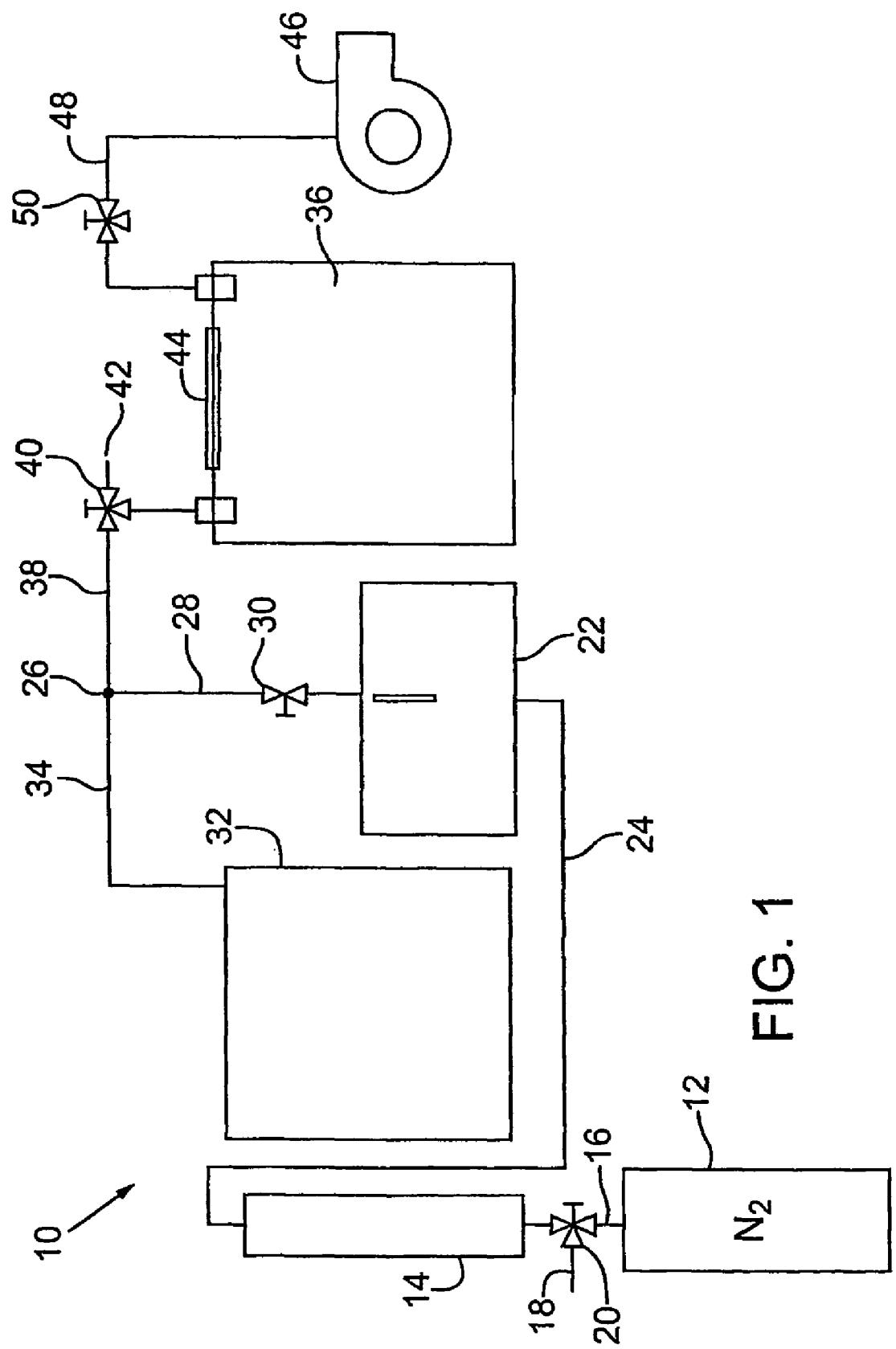
FIG. 1 is a schematic diagram of an exemplary apparatus for decontamination of a porous article.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprises" means "includes." Hence "comprising A or B" means including A, or B, or A and B. Although methods and materials similar or equivalent to those described herein can be used in the practice or testing of the present disclosure, suitable methods and materials are described below. In addition, the materials, methods, and examples are illustrative only and not intended to be limiting.

Abbreviations
  atm atmosphere
  cc cubic centimeter
  cm centimeter
  $ClO_2$ chlorine dioxide
  in. inches
  Hg mercury
  kg kilogram
  lb pound
  mbar millibar
  mL milliliter
  mm millimeter
  μm micrometer
  mtorr millitorr
  $N_2$ nitrogen
  $N/m^2$ Newtons per square meter
  Pa pascal
  PSI pounds per square inch
  WG water gauge Ambient: Condition of the environment, such as the temperature, humidity, or pressure present within a sealed environment, such as a sealed room or building. In particular examples, ambient temperature in a sealed environment is about 68° F. to about 72° F., ambient humidity in a sealed environment is the humidity in the absence of a humidifier, and the ambient pressure in a sealed environment is the pressure in the absence of a vacuum.

Autoclave: A device for heating substances above their boiling point, often used to manufacture chemicals or sterilize surgical instruments. In some examples, an autoclave is used as a decontamination chamber for decontaminating bioweapon-contaminated articles.

Bacillus: A genus of bacteria whose collective features include degradation of most substrates derived from plant and animal sources, including cellulose, starch, pectin, proteins, agar, hydrocarbons, and others; antibiotic production; nitrification; denitrification; nitrogen fixation; facultative lithotrophy; autotrophy; acidophily; alkaliphily; psychrophily, thermophily and parasitism. Spore formation, universally found in the genus, is thought to be a strategy for survival in the soil environment, wherein the bacteria predominate. Aerial distribution of dormant spores likely explains the occurrence of Bacillus species in most habitats examined.

There are more than 40 recognized species in the genus Bacillus (Bergey's Manual of Systematic Bacteriology Vol 2 (1986)). These include, but are not limited to, *B. acidocaldarius, B. alkalophilus, B. alvei, B. anthracis, B. azotoformans, B. badius, B. brevis, B. cereus, B. circulans, B. coagulans, B. fastidiosis, B. firmus, B. globisporus, B. insolitus, B. larvae, B. laterosporus, B. lentimorbus, B. lentus, B. licheniformis, B. macerans, B. macquariensis, B. marinus, B. megaterium, B. mycoides, B. pantothenticus, B. pasteurii, B. polymyxa, B. popillia, B. pumilus, B. schlegelii, B. sphaericus, B. stearothermophilus, B. subtilis,* and *B. thuringiensis*. In one specific, non-limiting example, a Bacillus is *Bacillus anthracis*, the agent that causes Anthrax.

Bacteria: Any of various prokaryotic organisms, including organisms within various phyla in the Kingdom Procaryotae. The terms encompass all microorganisms commonly regarded as bacteria, including *Mycoplasma, Chlamydia, Actinomyces, Streptomyces*, and *Rickettsia*. The term also includes *cocci, bacilli, spirochetes, spheroplasts, protoplasts*, and so forth. Spore-forming or sporulating bacteria are bacteria that are capable of forming spores (small, usually single-celled reproductive bodies that are highly resistant to desiccation and heat and are capable of growing into a new organism). Spore-forming bacteria include, but are not limited to members of the genera *Bacillus, Clostridium, Desulfotomaculans, Sporolactobacillus,* and Sporpsarcina.

Biological weapon or bioweapon: Any of various bacteria, viruses, and toxins that is or can be dispersed deliberately to cause disease or death to humans, animals, or plants, or other biological organisms. Examples of biological weapons include *Bacillus anthracis* that causes anthrax, *Yersinia pestis* that causes plague, and *Variola major* that causes smallpox. Biological weapons also include biotoxins, which any of various poisons produced by certain biological organisms, such as botulinum toxin, produced by the bacterium *Clostridium botulinum*, and ricin, from castor oil seeds. A sporulated bioweapon is a bioweapon that includes spores, for example bacterial spores.

Chlorine dioxide ($ClO_2$): A gas that is an extremely effective disinfectant, which rapidly inactivates pathogens such as bacteria, viruses, and parasites. Chlorine dioxide gas molecules can kill aerosolized, airborne pathogens, and also can diffuse through cracks and crevices in an article or a building or room and reach any surface that might have been reached by a pathogen. Chlorine dioxide gas has a greenish yellow color with a distinctive odor similar to that of chlorine. Chlorine dioxide is highly soluble in water but, unlike chlorine, chlorine dioxide does not react with water. It exists in aqueous solution as a dissolved gas.

A source of chlorine dioxide is any device that stores, releases, or produces chlorine dioxide. One type of a chlorine dioxide source is a chlorine dioxide generator. A chlorine dioxide generator is a device for producing chlorine dioxide gas, for example, a device that generates chlorine dioxide gas as needed. One such chlorine dioxide generator is the Saf-T-Chlor™ chlorine dioxide generator (CDG, Bethlehem, Pa.), which uses the reaction between dilute chlorine gas and thermally stable solid sodium chlorite to generate chlorine dioxide gas on demand. This reaction produces chlorine dioxide gas (in nitrogen), free of chlorite ion, chlorate ion or molecular chlorine.

Decontamination: To substantially inactivate or remove unwanted pathogens or pathogenic spores, for example by killing substantially 100% of pathogens present.

Decontamination gas: A gas effective to kill or otherwise substantially eliminate the pathogenicity of a pathogen, such as a sporulated pathogen, for example as, *Bacillus anthracis* spores. In a particular example, it is a gas that can kill or substantially eliminate the pathogenicity of weaponized spores. Examples of such decontamination gases include ethylene oxide, formaldehyde, steam, and chlorine dioxide.

Decontamination chamber: An enclosed space for decontaminating articles that are actually contaminated or suspected to be contaminated with spores. Decontamination chambers generally are capable of withstanding low atmospheric pressures, for example a pressure of at least as low as 100 (0.25396 $kg/cm^2$), 50 (0.12698 $kg/cm^2$), or even 29 inches of water (0.0736484 $kg/cm^2$). A decontamination chamber generally is also substantially gas-impermeable environment. Decontamination chambers include, but are not limited to sealed, rigid containers, autoclaves, hypobaric chambers.

In an example where a decontamination chamber is a room or building, the chamber is not subjected to low atmospheric pressures, but instead decontamination is performed at ambient pressure. Rooms or buildings can be sealed to prevent the influx or efflux of gas.

Humidification: The process of increasing the relative humidity, for example, by a humidifier. Examples of humidifiers include, but are not limited to evaporative humidifiers, steam humidifiers, and ultrasonic humidifiers. Humidity can be measured by a device known as a hygrometer.

Humidity: A measure of the amount of moisture present in a gas. Generally, the degree of humidity is expressed as relative humidity, or the ratio of the amount of water vapor in a gas at a specific temperature to the maximum amount that the gas could hold at that temperature, expressed as a percentage. A completely saturated gas is said to be at 100% relative humidity, and partial saturation is designated by smaller percentages, for example, 95%, 85%, 75%, 50%, or even less relative humidity.

Hypobaric chamber: A chamber in which the pressure is below atmospheric pressure, such as below 1 atmosphere. In some examples, a hypobaric chamber is used as a decontamination chamber, for example for decontaminating a porous article.

Porous: Having pores, cracks, or crevices. A porous article admits the passage of gas or liquid into or through pores or interstices. In general, a porous article is more difficult to effectively decontaminate than a non-porous article. A porous article includes, but is not limited to a cellulose, nitrocellulose, glass, polyester, nylon, and polyethylsulphone article. One specific, non-limiting example of a porous material is paper. Non-porous materials include, but are not limited to metal, glass, non-porous ceramics, and plastic.

Pressure: A measure of force/area. Atmospheric pressure is pressure caused by the weight of the atmosphere. At sea level it has a mean value of one atmosphere but reduces with increasing altitude. Atmospheric pressure can be measured in a variety of different units, for example: one atmosphere is equivalent to 1.01295 bars, $1.01295 \times 10^6$ dynes/cm, 29.9213 inches of mercury, 406.86 inches of water, 1.03325 kg/cm$^2$, 1012.95 mbar, $7.6 \times 10^5$ mtorr, $7.6 \times 10^5$ microns of mercury, $1.01296 \times 10^5$ Pa, $1.01296 \times 10^5$ N/m$^2$, 14.696 PSI, 14.696 lb/in$^2$, 760 torr, or 760 mm mercury.

In one example, pressure is created in an environment with a vacuum generator. In particular examples, the pressure is at least as low as 100, 80, 60, 50, 40, 30, or even 29 inches of water. For comparison, a pressure of 100 inches of water is equivalent to about 0.2458 atmospheres, or about 0.25396 kg/cm$^2$. A pressure of 80 inches of water is equivalent to about 0.19664 atmospheres, or about 0.203168 kg/cm$^2$. A pressure of 60 inches of water is equivalent to about 0.14748 atmospheres, or about 0.152367 kg/cm$^2$. A pressure of 50 inches of water is equivalent to about 0.1229 atmospheres, or about 0.12698 kg/cm$^2$. A pressure of 40 inches of water is equivalent to about 0.09832 atmospheres, or about 0.101584 kg/cm$^2$. A pressure of 100 inches of water is equivalent to about 0.07374 atmospheres, or about 0.076188 kg/cm$^2$. And, a pressure of 29 inches of water is equivalent to about 0.071282 atmospheres, or about 0.0736484 kg/cm$^2$.

Rigid container: A container that is capable of withstanding a vacuum pressure, for example a vacuum pressure of 100 (0.25396 kg/cm$^2$), 50 (0.12698 kg/cm$^2$), or even 29 inches of water (0.0736484 kg/cm$^2$).

Rotometer: A device for measuring the rate of fluid flow. In some examples, a rotometer is a tapered, vertical tube having a circular cross section in which a float moves in a vertical path to a height dependent on the rate of fluid flow through the tube.

Seal: A substantially gas-impermeable closure. A sealed environment, sealed room, or sealed building is one in which substantially all leaks have been blocked (for example, using plastic or other sheeting, tape, or caulking) to form an environment that is substantially gas-impermeable. A sealed environment (such as a sealed article, sealed room, or sealed building) can include one or more ports that permit agents to be moved in and out of the sealed area.

Spore: A small, usually single-celled reproductive body that is highly resistant to desiccation and heat and is capable of growing into a new organism, produced especially by certain bacteria, fungi, algae, and non-flowering plants. Spores have proven to be the most durable type of cell found in nature, and in their cryptobiotic state of dormancy, they can remain viable for extremely long periods of time, perhaps millions of years. Spores do not form normally during active growth and cell division. Rather, their differentiation begins when a population of vegetative cells passes out of the exponential phase of growth, usually as a result of nutrient depletion. Typically, one spore is formed per vegetative cell. In some examples, the mature spore is liberated by lysis of the mother cell (sporangium) in which it was formed.

Mature spores have no detectable metabolism, a state that is described as cryptobiotic. They are highly resistant to environmental stresses such as high temperature (some endospores can be boiled for several hours and retain their viability), irradiation, strong acids, disinfectants, etc. Although cryptobiotic, they retain viability indefinitely such that under appropriate environmental conditions, they germinate into vegetative cells.

Vacuum: An environment that has a reduced atmospheric pressure. A vacuum generator is a device that creates a reduced atmospheric pressure, for example in a decontamination chamber.

Viable: Capable of living, developing, or germinating under favorable conditions. For example, a viable spore is capable of developing under favorable conditions.

Weaponized: Enhancement of a bioweapon, for example by creating a finely dispersed, highly concentrated, easily aerosolized, and sterilization- or decontamination-resistant spore. Weaponization decreases a pathogen's (such as a spore's) susceptibility to decontamination.

Method for Decontamination

Disclosed herein are methods for decontaminating porous and non-porous articles or objects that are actually or potentially contaminated with spores. Unlike many conventional methods of decontamination, which often are ineffective at killing weaponized spores, such as weaponized spores on porous objects, in particular examples the present method includes humidification prior to the application of a deep vacuum, which is followed by the application of chlorine dioxide gas (which is in some examples concurrent with humidification). The humidification step enhances the susceptibility of spores (such as weaponized spores) to subsequent decontamination with chlorine dioxide. Application of the deep vacuum then allows the chlorine dioxide gas to penetrate the porous article more effectively. These factors act in concert to ensure that the article is fully decontaminated, even when the article is porous and the spores are weaponized.

The method includes enclosing the article in an environment, humidifying the environment to enhance the susceptibility of the spores to subsequent decontamination with a decontamination gas (such as chlorine dioxide), reducing the pressure in the humidified environment, for example to a vacuum pressure such as at least as low as 100 inches of water (0.25396 kg/cm$^2$) to enhance penetration of the decontamination gas into the article, and then introducing into the environment a concentration of the decontamination gas effective to decontaminate the article by killing substantially 100% of the spores.

The method can be carried out using any rigid, substantially gas-impermeable chamber as a decontamination chamber, for example a container that can withstand pressures below atmospheric pressure, such as below 1 atmosphere, for example below 0.2458 atmosphere, without compromising the structural integrity of the chamber. Particular examples of decontamination chambers include, but are not limited to: rigid containers, such as an autoclave or a hypobaric chamber. The vacuum pressure applied to the humidified environment can be adjusted to suit the particular needs of a decontamination project. For example, in certain examples, the pressure in the humidified environment is reduced to a pressure even lower than 100 inches of water (0.25396 kg/cm$^2$), for example at least as low as 50 inches of water (0.12698 kg/cm$^2$), or at least as low as 29 inches of water (0.0736484 kg/cm$^2$).

In examples where the decontamination chamber is a room or building, the same methods are used, except that no deep vacuum is applied. Instead, the room or building is at a pressure that does not compromise the structural integrity of the room or building. The room or building can be under a vacuum, as long as the resulting pressure does not compromise the structural integrity of the room or building, for example does not cause implosion of the room or building. In particular examples, the room or building is at ambient pressure, such as atmospheric pressure. The method can include sealing the room or building to form a sealed environment, and can further include reinforcing one or more windows or other openings.

The method also includes humidifying the environment to enhance the susceptibility of the spores to subsequent decontamination with a decontamination gas, such as chlorine dioxide. In some embodiments, humidifying the environment includes increasing the relative humidity of the environment to at least 90%. In particular examples, the relative humidity of the environment is increased to at least 90% for a defined period of time, for example at least one hour or at least three hours.

The concentration of the decontamination gas (such as chlorine dioxide) also can be varied to suit the needs of a particular decontamination project. For example, in some embodiments the concentration of gaseous chlorine dioxide is at least 1000 parts per million, for example at least 2500 parts per million. In some examples, the decontamination gas exposure time is adjusted For instance, in some examples, the article is exposed to a decontamination gas for at least one hour, for at least three hours, or for at least six hours. In particular examples, the decontamination gas is provided with humidification, such as concurrent humidification of at least 70% humidity, such as at least 80% humidity, or even at least 90% humidity.

The method can be used to decontaminate various types of articles that are actually or potentially contaminated with various types of spores. For example, in particular examples, the spore is a *Bacillus anthracis* spore. In even more particular examples, the spore is a weaponized spore. In some examples, the article is paper.

In some examples, the environment is a decontamination chamber, humidifying the environment includes increasing the relative humidity of the environment to at least 90% for at least one hour, the pressure in the humidified environment is reduced to at least as low as 29 inches of water (0.0736484 kg/cm$^2$), the concentration of the decontamination gas (such as gaseous chlorine dioxide) is at least 1000 parts per million, and the article is exposed to the gaseous chlorine dioxide for at least one hour. In particular examples, the chlorine dioxide is delivered with at least 90% humidification.

In other examples, the environment is a room or building, and enclosing the article in an airtight environment involves sealing the room or building, humidifying the environment involves increasing the relative humidity of the environment to at least 90% for at least one hour, the concentration of gaseous chlorine dioxide is at least 1000 parts per million, and the article is exposed to the gaseous chlorine dioxide for at least one hour. In particular examples, the chlorine dioxide is delivered with at least 90% humidification.

In one particular example, the method is a method of decontaminating a porous article, and the method includes enclosing the article in a decontamination chamber, increasing the relative humidity in the decontamination chamber to at least 95%, reducing the pressure in the humidified decontamination chamber to at least as low as 50 inches of water (0.12698 kg/cm$^2$), and then introducing into the decontamination chamber at least 1000 parts per million of the decontamination gas, thus decontaminating the article by killing substantially 100% of the spores. In particular examples, the decontamination gas is delivered with at least 90% humidification.

In another particular example, the method is a method of decontaminating a porous article, and the method includes enclosing the article in a sealed room or building, increasing the relative humidity in the sealed room or building to at least 95%, and then introducing into the room or building at least 1000 parts per million of the decontamination gas, for example with concurrent at least 95% humidification, thus decontaminating the article by killing substantially 100% of the spores.

Apparatus

Also disclosed herein is an apparatus for decontaminating a porous article. The apparatus includes a selectively sealable decontamination chamber, a decontamination chamber humidifier, a source of decontamination gas (such as chlorine dioxide) in fluid communication with the decontamination chamber, and in some examples a decontamination chamber vacuum generator. In some embodiments, the apparatus also includes a first fluid flow path for transferring humidified gas from the decontamination chamber humidifier to the selectively sealable decontamination chamber, a second fluid flow path for transferring decontamination gas from the source of the gas to the selectively sealable decontamination chamber, and in some examples a third fluid flow path for evacuating the selectively sealable decontamination chamber via the decontamination chamber vacuum generator. In some embodiments, the apparatus also includes a flow regulator in the first fluid flow path, or a rotometer in the first fluid flow path.

The apparatus can also include a nitrogen source and a fourth fluid flow path for transferring nitrogen gas to the decontamination chamber humidifier. In some examples, the apparatus also includes a fill valve or a flow regulator in the fourth fluid flow path. In particular examples, the apparatus also includes a flow regulator in the third fluid flow path, and in other examples the apparatus also includes a ventilation valve in the second fluid flow-path.

When the decontamination gas is chlorine dioxide, the chlorine dioxide source can be any source of chlorine dioxide known in the art. For example, in some embodiments, the chlorine dioxide source is a chlorine dioxide generator. In particular examples, the chlorine dioxide generator is a Saf-T-Chlor™ chlorine dioxide generator.

In some embodiments, the selectively sealable decontamination chamber is a rigid container. In particular examples, the apparatus also includes a heat source for providing heat to the selectively sealable decontamination chamber. Some embodiments of the apparatus also include a hygrometer for regulating humidity in the selectively sealable decontamination chamber.

In particular examples of the apparatus, the rigid container includes a heat source, a thermostat for regulating the heat source, and a hygrometer for regulating humidity in the selectively sealable decontamination chamber.

The decontamination chamber can be any rigid, substantially gas-impermeable chamber, for example an autoclave or a hypobaric chamber that can withstand a vacuum pressure of at least as low as 100 inches of water (0.25396 kg/cm$^2$), at least as low as 50 inches of water (0.12698 kg/cm$^2$), or at least as low as 29 inches of water (0.0736484 kg/cm$^2$). In other examples, the decontamination chamber is a sealed room or a sealed building under a pressure that does not compromise the structural integrity of the room or building. The apparatus can also include a heat source for providing heat to the decontamination chamber, or a hygrometer for regulating humidity in the selectively sealable decontamination chamber.

DESCRIPTION OF SEVERAL SPECIFIC EMBODIMENTS

Decontamination of Porous Articles/Objects

Disclosed herein are methods for decontaminating porous and non-porous articles or objects. Many known methods of bioweapon decontamination, for instance exposure to chlorine dioxide, ethylene oxide, formaldehyde, or steam, are effective at decontaminating non-porous articles, for example non-porous glass, porcelain, and metals. However, terrorist activities have targeted the United States mail system, generating numerous anthrax-contaminated parcels and envelopes, as well as mail-handling equipment, furniture, office supplies, and the like. Conventional decontamination techniques are ineffective at decontaminating such porous articles because the sterilant fails to penetrate deeply enough into the pores of the articles to fully inactivate all contaminating spores.

By contrast, the methods disclosed herein can include subjecting the contaminated article (such as a porous article) to a deep vacuum prior to exposure to the sterilant gas. This permits the gas to penetrate the article more fully, exposing the spores contained in inner pockets and pores to the gas, which creates a greater mass transfer of gas and results in a thorough decontamination of the article. The deep vacuum is equivalent to a pressure of at least as low as 100, 80, 60, 50, 40, 30, or even 29 inches of water. For comparison, a pressure of 100 inches of water is equivalent to about 0.2458 atmospheres, or about 0.25396 kg/cm$^2$. A pressure of 80 inches of water is equivalent to about 0.19664 atmospheres, or about 0.203168 kg/cm$^2$. A pressure of 60 inches of water is equivalent to about 0.14748 atmospheres, or about 0.152367 kg/cm$^2$. A pressure of 50 inches of water is equivalent to about 0.1229 atmospheres, or about 0.12698 kg/cm$^2$. A pressure of 40 inches of water is equivalent to about 0.09832 atmospheres, or about 0.101584 kg/cm$^2$. A pressure of 100 inches of water is equivalent to about 0.07374 atmospheres, or about 0.076188 kg/cm$^2$, and a pressure of 29 inches of water is equivalent to about 0.071282 atmospheres, or about 0.0736484 kg/cm$^2$.

The pressure employed in a particular situation can be tailored to suit any of a variety of factors, for example, the type of decontamination chamber, room, or building to be decontaminated, the porosity of the article or articles to be contaminated, the concentration of chlorine dioxide gas used, the amount of humidification desired, the contaminating pathogen present (or thought to be present), or the length of time the article is exposed to the sterilant gas.

Decontamination of Weaponized Spores

Conventional decontamination techniques, while effective at inactivating many types of bacterial spores, often are ineffective at killing weaponized spores. Among other modifications, weaponized spores are usually desiccated, which makes them particularly resistant to chemical sterilizing agents. Thus, articles contaminated with desiccated spores often require decontamination with substantially more rigorous sterilization conditions (for instance, a higher sterilant concentration or longer exposure time) than do non-desiccated spores.

The methods disclosed herein overcome this problem by including a humidification step that enhances the susceptibility of desiccated spores to inactivation with decontaminating gas, such as chlorine dioxide. For example, by enhancing the susceptibility of the spores to the chlorine dioxide sterilant, a lower concentration of chlorine dioxide may be used, or the length of exposure to the chlorine dioxide may be shortened. Humidification of the spores can be accomplished by pre-humidifying the article to be decontaminated in an atmosphere of controlled humidity prior to or concurrent with exposing the article to the chlorine dioxide gas. Generally, the degree of humidity is expressed as relative humidity, or the ratio of the amount of water vapor in a gas at a specific temperature to the maximum amount that the gas could hold at that temperature, expressed as a percentage. A completely saturated gas is said to be at 100% relative humidity, and partial saturation is designated by smaller percentages, for example, 95% or even less relative humidity.

In some examples, the humidification step is carried out at a relative humidity of at least 70%, at least 80%, at least 90%, at least 95%, at least 98%, or even greater relative humidity. In some embodiments, the article is exposed to the elevated humidity for at least 15 minutes, at least 30 minutes, or at least 1, at least 2, at least 3, at least 5, at least 10, or at least 20 hours. The relative humidity chosen and the duration of exposure to the relative humidity can be optimized to suit a particular decontamination project, and can vary depending on, for example, the type of decontamination chamber, room, or building to be decontaminated, the porosity of the article or articles to be contaminated, the concentration of decontaminating gas used, the pathogen (such as a spore) present or thought to be present, or the length of time the article is exposed to the sterilant gas. In certain examples, the humidity in the decontamination chamber is raised to a relative humidity of at least 70%, at least 80%, at least 90%, at least 95%, at least 98%, or even greater, during exposure of the article to the sterilant gas.

In some examples, the humidification step is carried out at room temperature (such as 65° F.-74° F., for example 68° F.-72° F., such as 68° F., 69° F., 70° F., 71° F., or 72° F.), although lower or higher temperatures can be employed if desired or necessary. In some examples, the humidification step is carried out at an elevated temperature, for example at least 75° F., at least 85° F., at least 95° F., or higher. Although the humidification step generally is carried out using humidified air, other humid gases, such as humidified nitrogen gas, can be used. The humidification step can be performed before introduction of the decontaminating gas, during introduction of the decontaminating gas, following introduction of the decontaminating gas, or combinations thereof.

Figure 3:
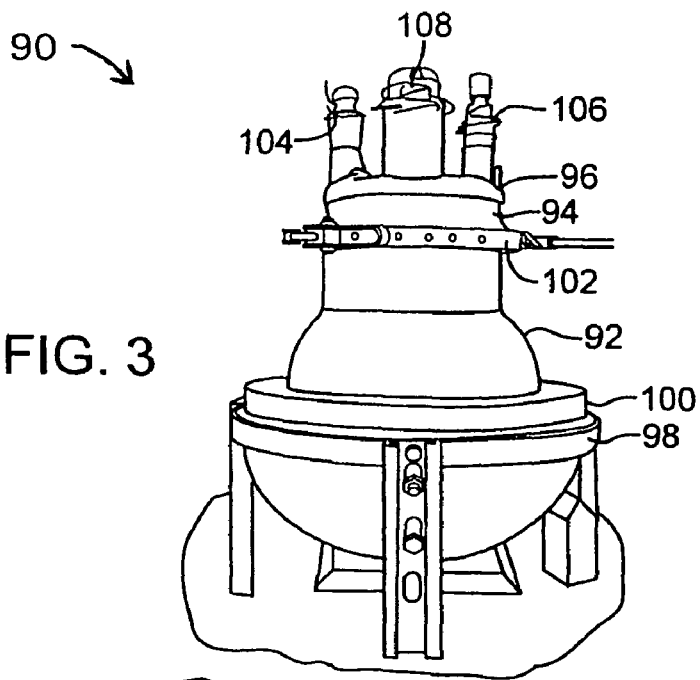
FIG. 3 is a diagram of an exemplary rigid container for use as a selectively sealable decontamination chamber in the apparatus of FIG. 1.

In certain examples, the decontamination chamber is a rigid container, for example as shown in FIG. 3. Such an embodiment is particularly suited to decontaminating small articles, such as mail envelopes or parcels. In such an embodiment, a suitably-sized article, for example a piece of mail or a parcel, is placed in the rigid container, and the container is sealed prior to exposing the article to chlorine dioxide gas.

In other examples, the decontamination chamber is an autoclave or hypobaric chamber. Such an embodiment is particularly suited to the decontamination of medium or large-sized articles. In one particular, non-limiting example, an autoclave or hypobaric chamber is used for the decontamination of mail, either as individual pieces or as multiple items in larger containers, such as in trays, baskets, or bins. In some embodiments, the trays, baskets, or bins are placed onto wheeled racks, or transported by automated means or fork lifts, or transported by any other method of holding and transporting batches of mail, and the carts or forkiifts are wheeled into the autoclave or is hypobaric chamber. The autoclave or hypobaric chamber is then sealed prior to exposing the article(s) to chlorine dioxide gas.

The decontamination chamber can also be a room or a building (see FIG. 4), for example a room or building contaminated or thought to be contaminated with a weaponized spore. This embodiment is particularly useful for decontaminating rooms or buildings contaminated with weaponized spores, for example when such rooms or buildings contain porous articles, for example paper.

In particular examples, the room or building is sealed to form a sealed environment. Sealing the room or building prevents the escape of the decontaminating gas (such as chlorine dioxide) to the atmosphere. Sealing the room or building can include, but is not limited to, sealing the windows with foil-backed foam insulation, sealing cracks with expanding foam or silicone caulking, and sealing skylights, loading docks, and building openings with poly-sheeting and foil tape. In even more particular examples, one or more windows in the room or building are reinforced prior to decontamination.

Chlorine Dioxide

The particular decontamination gas used in certain examples is chlorine dioxide, a relatively small, volatile and highly energetic molecule. Chlorine dioxide gas is unstable at high concentrations; generally, it is generated at the point of use.

Chlorine dioxide is an extremely effective disinfectant, which rapidly inactivates bacteria, viruses, and parasites such as *Giardia* and *Cryptosporidium*. Because chlorine dioxide oxidizes but does not chlorinate, chlorinated organic by-products (for example, trihalomethanes, haloacetic acids, dioxins, and furans) typically are not produced. Neither does chlorine dioxide produce appreciable amounts of aldehydes, ketones, ketoacids, or other problematic compounds associated with oxidation of organic matter by other, less selective means.

In addition, under the correct reaction conditions (such as delivery into an environment of at least 70% humidity, or delivery with at least 70% humidification), chlorine dioxide inactivates bacterial spores, for example *Bacillus anthracis* spores. High-purity chlorine dioxide gas is an excellent gas-phase decontaminating agent, because chlorine dioxide gas molecules can kill aerosolized, airborne pathogens, and also can diffuse through cracks and crevices in an article or a room or building and reach any surface that might have been reached by the target pathogen.

Chlorine dioxide gas can be prepared by any of the methods known in the art. One such method involves passing a stream of air-diluted chlorine gas or nitrogen-diluted chlorine gas at a metered rate through a column of finely divided sodium chlorite, and into a partially evacuated chamber. This procedure is described more fully in Grubitsch et al., *Monatsh.,* 93:246 (1962).

Another method of preparing chlorine dioxide gas is the reaction of sodium chlorite solutions in the presence of acids. In one embodiment, a dilute solution of aqueous potassium persulfate is treated with a dilute solution of aqueous sodium chlorite at ambient temperatures (20-30° C.) in a closed reaction vessel. This method is discussed more fully in Rosenblatt et al., *J. Org. Chem.,* 28:2790 (1963).

Chlorine dioxide gas can also be delivered via a chlorine dioxide source, which can be any device that stores, releases, or produces chlorine dioxide. One type of a chlorine dioxide source is a chlorine dioxide generator. A chlorine dioxide generator is a device for producing chlorine dioxide gas, for example, a device that generates chlorine dioxide gas as needed. One such chlorine dioxide generator is the CDG Saf-T-Chlor™ chlorine dioxide generator (CDG, Bethlehem, Pa.), which uses the reaction between dilute chlorine gas and thermally stable solid sodium chlorite to generate chlorine dioxide gas on demand:

$$Cl_2(gas)+NaClO_2(solid)\rightarrow 2ClO_2(gas)+NaCl(solid)$$

This reaction produces chlorine dioxide gas (in nitrogen), free of chlorite ion, chlorate ion or molecular chlorine.

CDG Gas: Solid chlorine dioxide generators are available in at least two sizes: bench-scale generators for smaller scale applications and plant-scale generators, which are useful for providing chlorine dioxide in amounts sufficient to decontaminate large areas, or for the routine decontamination of large volumes of mail.

In some embodiments, the chlorine dioxide gas is delivered to the decontamination chamber in the form of a gaseous mixture of chlorine dioxide, an inert carrier gas, and moisture in the form of humidity. One specific, non-limiting example of an inert carrier gas is nitrogen gas. In some embodiments, the chlorine dioxide gas is delivered to the decontamination chamber in the form of a gaseous mixture of chlorine dioxide and air, such as air that is at least 70%, or even at least 90% humidity.

The concentration of chlorine dioxide can be varied to suit the needs of a particular decontamination project. In some examples, the concentration of gaseous chlorine dioxide is at least 1,000 parts per million, such as at least 1,500, at least 2,000, at least 2,500, at least 3,000, or at least 3,500 parts per million. In some embodiments, the chlorine dioxide exposure time is adjusted. For instance, in some examples, the article is exposed to the gaseous chlorine dioxide for at least one hour, for at least three hours, or for at least six hours. The particular concentration of chlorine dioxide in the carrier gas selected for use is a function of several factors, including the inherent ability of the particular spores to resist decontamination by chlorine dioxide, the duration of exposure to the chlorine dioxide gas, the degree to which the spores are desiccated, the humidity to which the article has been exposed during the humidification step, the duration of the humidification step, and the relative humidity of the chlorine dioxide/carrier gas.

Apparatus for Decontamination of Porous Articles

Also disclosed herein is an apparatus for decontaminating porous articles. One embodiment of the apparatus 10 is shown in FIG. 1. Apparatus 10 includes a nitrogen source 12 in fluid communication with a decontamination chamber humidifier 14 and a first fluid flow path 16 for transferring nitrogen gas to decontamination chamber humidifier 14. First fluid low path 16 includes a fill valve 18, which permits the addition of gas or liquid to first fluid flow path 16, and a flow regulator 20, which regulates flow of the nitrogen gas to decontamination chamber humidifier 14.

Decontamination chamber humidifier 14 is in fluid communication with a rotometer 22 via a second fluid flow path 24. Rotometer 22 is in fluid communication with one inlet of a T junction 26 via a third fluid flow path 28. Third fluid flow path 28 includes a flow regulator 30, which regulates flow of the humidified nitrogen gas to T junction 26.

Apparatus 10 also includes a source of chlorine dioxide gas 32, which is in fluid communication with the second inlet of T junction 26 via fourth fluid flow path 34. The outlet of T junction 26 is in fluid communication with a selectively sealable decontamination chamber 36 via a fifth fluid flow path 38. Fifth fluid flow path 38 includes a flow regulator 40, which regulates flow of a mixture of chlorine dioxide gas and nitrogen gas from T junction 26 to selectively sealable decontamination chamber 36, and a ventilation valve 42, which permits the influx or efflux of gas from fifth fluid flow path 38.

Selectively sealable decontamination chamber 36 accommodates one or more articles for decontamination, and includes a lid 44 that can be opened or closed as desired. When closed, lid 44 forms a gas-tight closure. Selectively sealable decontamination chamber 44 is in fluid communication with a vacuum generator 46 via a sixth fluid flow path 48. Sixth fluid flow path 48 includes a flow regulator 50, which regulates flow of exhaust gas from selectively sealable decontamination chamber 36 to vacuum generator 46.

In operation, an article in need of decontamination is enclosed in selectively sealable decontamination chamber 36. Lid 44 is then sealed to form a gas-impermeable seal, and humidification of decontamination chamber 36 is initiated. Nitrogen gas from nitrogen source 12 flows through first fluid path 16 to decontamination chamber humidifier 14, where the nitrogen gas is humidified. Flow regulator 20 regulates the pressure of the nitrogen gas in first fluid flow path 16.

Humidified nitrogen gas flows from decontamination chamber humidifier 14 to rotometer 22 through second fluid flow path 24. Humidified nitrogen gas then flows from rotometer 22 through third fluid flow path 28 to the first inlet of T junction 26, out the outlet of T junction 26, and through fifth fluid flow path 38 to selectively sealable decontamination chamber 36. The article is incubated in the humidified nitrogen gas for a predetermined time. The relative humidity of the humidified nitrogen gas and the duration of incubation are determined based on the particular characteristics of the article being decontaminated, including, but not limited to, the porosity of the article, the inherent ability of potential or actual contaminating spores to resist decontamination by chlorine dioxide, the concentration of chlorine dioxide gas to be used, the degree to which potential or actual contaminating spores are desiccated, and the relative humidity of the chlorine dioxide/nitrogen gas mixture to be used.

After incubation, the humidified nitrogen gas is exhausted from selectively sealable decontamination chamber 36 by vacuum generator 46 through sixth fluid flow path 48. Vacuum generator 46 continues to remove gas from selectively sealable decontamination chamber 36 until a desired vacuum pressure is achieved in selectively sealable decontamination chamber 36, for example a vacuum pressure equivalent to at least as low as 100, 50, or 29 inches of water.

Following the humidification steps a decontamination step begins. Nitrogen gas from nitrogen source 12 flows through first fluid path 16 to decontamination chamber humidifier 14, where the nitrogen gas is humidified. Humidified nitrogen gas flows from decontamination chamber humidifier 14 to rotometer 22 through second fluid flow path 24. Humidified nitrogen gas then flows from rotometer 22 through third fluid flow path 28 to the first inlet of T junction 26. Chlorine dioxide gas from source 32 passes from source of chlorine dioxide gas 32 through fourth fluid flow path 34 to the second inlet of T junction 26. The chlorine dioxide gas combines with the humidified nitrogen gas in T junction 26 to form a chlorine dioxide/nitrogen gas mixture with a desired chlorine dioxide concentration, for instance 1,000 ppm or 2,500 ppm chlorine dioxide gas in humidified nitrogen gas. The particular concentration of chlorine dioxide in the carrier gas selected for use is a function of several factors, including, but not limited to, the porosity of the article, the inherent ability of the particular spores to resist decontamination by chlorine dioxide, the duration of exposure to the chlorine dioxide gas, the degree to which the spores are desiccated, the humidity to which the article has been exposed during the humidification step, the duration of the humidification step, and the relative humidity of the chlorine dioxide/nitrogen gas mixture.

The chlorine dioxide/nitrogen gas mixture then flows from the outlet of T junction 26 into selectively sealable decontamination chamber 36 via fifth fluid flow path 38. The article is incubated in the chlorine dioxide/nitrogen gas mixture for a predetermined time, which is chosen based on a number of factors, including, but not limited to, the porosity of the article, the inherent ability of the particular spores to resist decontamination by chlorine dioxide, the concentration of chlorine dioxide gas, the degree to which the spores are desiccated, the humidity to which the article has been exposed during the humidification step, and the relative humidity of the chlorine dioxide/nitrogen gas mixture.

After the appropriate incubation period, the chlorine dioxide/nitrogen gas mixture is then evacuated from selectively sealable decontamination chamber 36 by decontamination chamber vacuum generator 46 via sixth fluid flow path 48. Flow regulator 50 regulates the pressure of the chlorine dioxide/nitrogen gas mixture in sixth fluid flow path 48.

Chlorine dioxide generator

Figure 2:
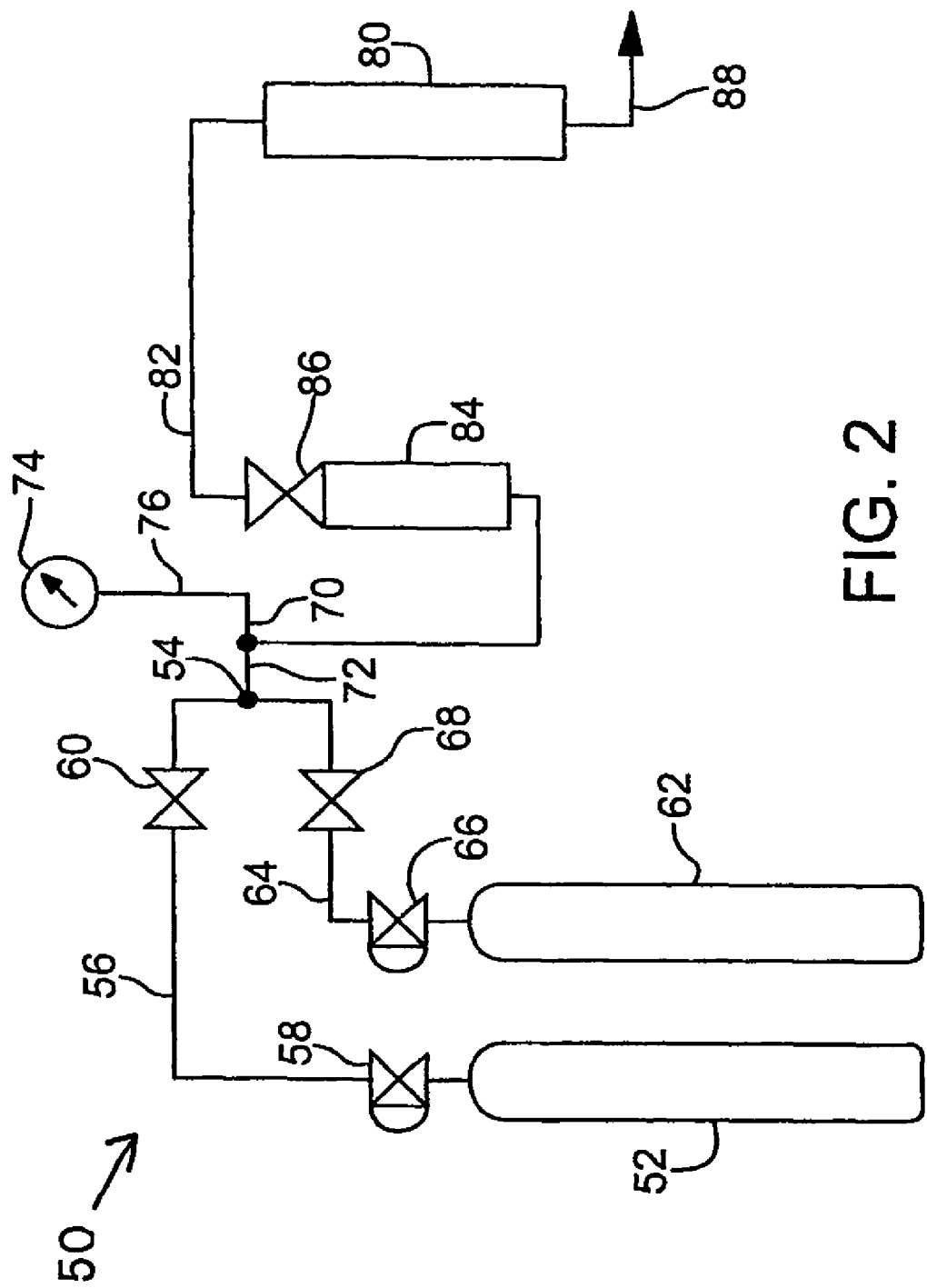
FIG. 2 is a schematic diagram of an exemplary chlorine dioxide generator for use in the apparatus of FIG. 1.

In some embodiments, source of chlorine dioxide gas 32 is a CDG Saf-T-Chlor™ chlorine dioxide gas generator 50, as shown in FIG. 2. CDG chlorine dioxide generator 50 includes a chlorine gas source 52 in fluid communication with a first inlet of first T junction 54 via first fluid flow path 56. First fluid flow path 56 includes a pressure regulator 58 and an on/off valve 60.

CDG chlorine dioxide generator 50 also includes a nitrogen tank 62 in fluid communication with a second inlet of first T junction 54 via second fluid flow path 64. Second fluid flow path 64 includes a pressure regulator 66 and an on/off valve 68.

The outlet of first T junction 54 is in fluid communication with a first inlet of second T junction 70 via third fluid flow path 72. A second inlet of T junction 70 is in fluid communication with a pressure gauge 74 via fourth fluid flow path 76. The outlet of second T junction 70 is in fluid communication with a sodium chlorite cartridge 80 via a fifth fluid flow path 82. Fifth fluid flow path 82 includes a flow meter 84 and a control valve 86. Chlorine dioxide gas from sodium chlorite cartridge 80 leaves CDG chlorine dioxide generator 50 via sixth fluid flow path 88.

To generate chlorine dioxide gas, on/off valve 60 is opened, and a mixture of chlorine and nitrogen gas is transferred from chlorine/nitrogen tank 52 to the first inlet of first T junction 54 via first fluid flow path 56.

On/off valve 68 is also opened, and nitrogen gas is transferred from chlorine/nitrogen tank 62 to the second inlet of first T junction 54 via second fluid flow path 64. Pressure regulator 58 regulates the pressure of the gas in second fluid flow path 64. The chlorine/nitrogen gas mixture combines with nitrogen gas in first T junction 54 to form a gas mixture. The gas mixture flows from the outlet of first T junction 54 to the first inlet of second T junction 70 via third fluid flow path 72. Pressure gauge 74 measures the pressure of the gas mixture via the second inlet of second T junction 70 and fourth fluid flow path 76.

The gas mixture is then transferred from second T junction 70 to sodium chlorite cartridge 80 via fifth fluid flow path 82, where it reacts with the sodium chlorite in sodium chlorite cartridge 80 to form chlorine dioxide gas. Flow meter 84 regulates the pressure of the gas mixture in fifth fluid flow path 82, and control valve provides a mechanism for interrupting gas flow through fifth fluid flow path 82, if needed. The chlorine dioxide gas flows from sodium chlorite cartridge 80 and exits chlorine dioxide generator 50 via sixth fluid flow path 88.

Decontamination Chambers

The selectively sealable decontamination chamber 36 described above (FIG. 1) can be any rigid, substantially gas-impermeable chamber, for example a rigid container, an autoclave, a hypobaric chamber, a room, or a building. In one embodiment, selectively sealable decontamination chamber 36 is a rigid container 90, as shown in FIG. 3. The rigid container 90 includes a reaction vessel 92 that has a sealable opening 94 and a lid 96 for sealing the sealable opening 94. Reaction vessel 92 is supported by a stand 98, which includes a heat source 100 for providing heat to reaction vessel 92.

Reaction vessel 92 is supported by a stabilizing collar 102. Lid 94 includes a first sealable port 104 and a second sealable port 106. A thermometer or a hygrometer can be introduced into reaction vessel 92 via first sealable port 104 or second sealable port 106. Lid 94 also includes a third sealable port 108 through which gas and liquid can be introduced to and removed from reaction vessel 92.

In operation, a suitably-sized article, for example a piece of mail or a parcel, is placed in reaction vessel 92, and sealable opening 94 is sealed using lid 96. Humidified gas is added to reaction vessel 92 via third sealable port 108, and the article is incubated in the humidified gas for a predetermined period of time. The relative humidity of the humidified gas and the duration of incubation are determined based on the particular characteristics of the article being decontaminated, including, but not limited to, the porosity of the article, the inherent ability of potential or actual contaminating spores to resist decontamination by chlorine dioxide, the concentration of chlorine dioxide gas to be used, the degree to which potential or actual contaminating spores are desiccated, and the relative humidity of the chlorine dioxide gas to be used.

The humidified gas is then evacuated via third sealable port 108, generating a vacuum pressure of at least as low as 100 inches of water. Chlorine dioxide gas is then added to reaction vessel 92 via the third sealable port 108, and the article is incubated in the chlorine dioxide gas for a predetermined time. The particular concentration of chlorine dioxide gas selected for use is a function of several factors, including, but not limited to, the porosity of the article, the inherent ability of potential or actual contaminating spores to resist decontamination by chlorine dioxide, the duration of exposure to the chlorine dioxide gas, the degree to which potential or actual contaminating spores are desiccated, the humidity to which the article has been exposed during the humidification step, the duration of the humidification step, and the relative humidity of the chlorine dioxide gas. The chlorine dioxide gas (such as humidified chlorine gas) is then evacuated via third sealable port 108, lid 96 is opened, and the article is removed from reaction vessel 92 through sealable opening 94.

Figure 4:
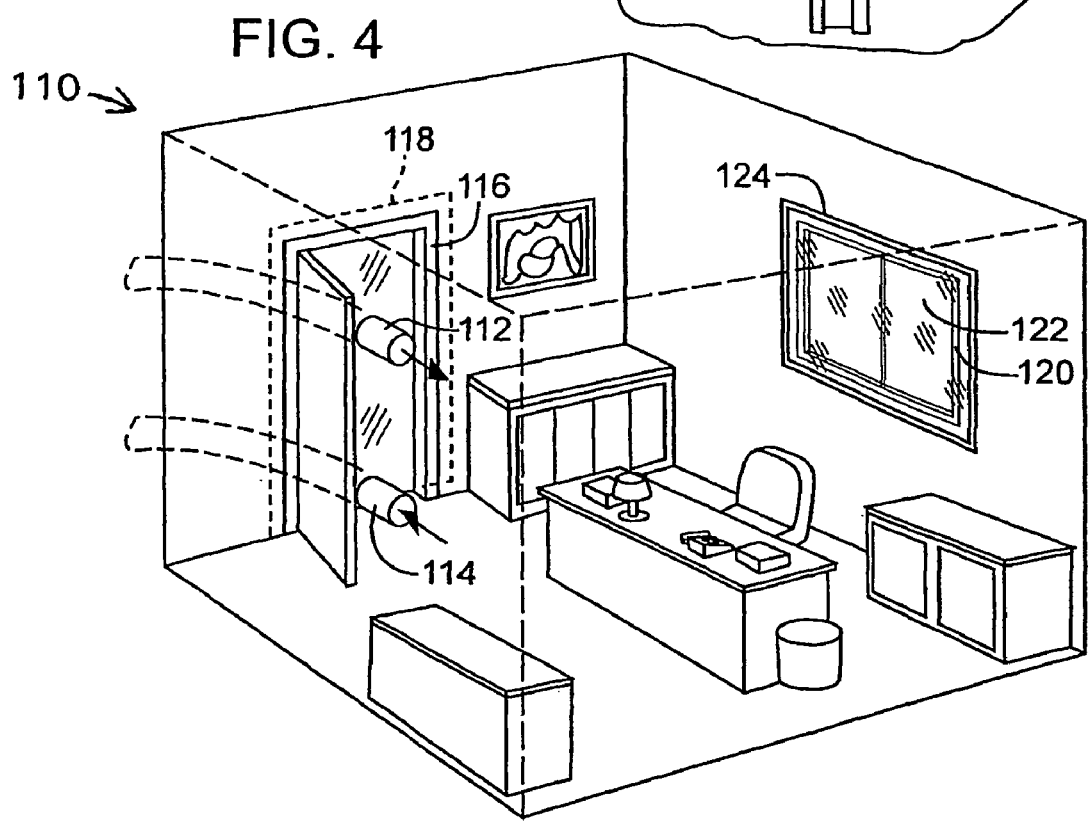
FIG. 4 is a diagram of an exemplary room that can provide the selectively sealable decontamination chamber of FIG. 1, except that the room would be at ambient pressure during the decontamination.

In another embodiment, as shown in FIG. 4, selectively sealable decontamination chamber 36 is a room 110. Room 110 includes an influx channel 112 for transferring gas into room 110, and an efflux channel 114 for transferring gas out of room 110. Influx channel 112 and efflux channel 114 can pass through a doorway 116 that is sealed with a vapor barrier 118. In particular examples, influx channel 112 and efflux channel 114 are a single channel, whose purpose changes depending on whether materials are introduced or moved from room 110. Room 110 can also include a window 120 that is sealed with a vapor barrier 122 and reinforced with a reinforcing panel 124. In examples were the selectively sealable decontamination chamber 36 is a room 110, a vacuum generator 46 is not required.

In operation, humidified gas (such as humidified air or humidified chlorine dioxide or both) is transferred into room 110 via influx channel 112. Room 110 is then incubated in the humidified gas for a predetermined period of time. The relative humidity of the humidified gas and the duration of incubation are determined based on the particular characteristics of room 110, including, but not limited to, the porosity of articles and furnishings in room 110, the inherent ability of potential or actual contaminating spores to resist decontamination by the gas used, the concentration of decontamination gas used, the degree to which the potential or actual contaminating spores are desiccated, and the relative humidity of the decontamination gas used.

If not administered previously, decontamination gas (such as humidified chlorine dioxide gas) is then transferred into room 110 via influx channel 112, and room 110 is incubated in the decontamination gas for a predetermined period of time. The particular concentration of decontamination gas selected for use is a function of several factors, including, but not limited to, the inherent ability of potential or actual contaminating spores to resist decontamination by the decontamination gas such as chlorine dioxide, the duration of exposure to the decontamination gas, the degree to which potential or actual contaminating spores are desiccated, the humidity to which the article has been exposed during the humidification step, the duration of the humidification step, and the relative humidity of the decontamination gas. The decontamination gas is then evacuated from room 110 via efflux channel 114.

EXAMPLE 1

Decontamination of Weaponized Spores with High-purity Chlorine Dioxide Gas

This example demonstrates that a concentration of 10,000 parts per million (ppm) chlorine dioxide gas is an effective sterilant for paper contaminated with weaponized spores.

Paper filters (n=16) contaminated with $2.0 \times 10^8$ weaponized spores were exposed to 10,000 ppm $ClO_2$ for four hours. Filters were cultured under permissive culture conditions (15 hour incubation in tryptic soy broth) to determine whether the weaponized spores were viable following the decontamination protocol. Out of 16 filters exposed to the decontamination protocol, none showed viable spores following decontamination. Thus, a concentration of 10,000 parts per million (ppm) chlorine dioxide gas is an effective sterilant for paper contaminated with weaponized spores.

EXAMPLE 2

Effect of Pre-humidification on Decontamination Efficacy

This example demonstrates that following a pre-humidification step carried out at 95% relative humidity and 95° F. for 1-3 hours, a concentration of 10,000 parts per million (ppm) chlorine dioxide gas is an effective sterilant for both conventional biological indicator spores and weaponized spores.

Paper filters contaminated with $2.0 \times 10^8$ weaponized spores (n=2), $10^{10}$ weaponized spores (n=2), or, $10^6$ conventional biological indicator spores (n=2) were enclosed in envelopes and pre-humidified at 95% relative humidity and 95° F. for 1-3 hours. They were then exposed to 10,000 ppm $ClO_2$ for four hours. Filters were cultured under permissive culture conditions (15 hour incubation in tryptic soy broth) to determine whether the spores were viable following the decontamination protocol. None of the filters showed viable spores following decontamination (Table 1.)

TABLE 1

Effect of pre-humidification on decontamination efficacy

| | Humidification time | | |
|---|---|---|---|
| | 1 hour | 2 hours | 3 hours |
| $2 \times 10^8$ Weaponized Spores/filter | 0/2 | 0/2 | 0/2 |
| $10^{10}$ Weaponized Spores/filter | 0/2 | 0/2 | 0/2 |
| $10^6$ Conventional Biological Indicator Spores/filter | 0/2 | 0/2 | 0/2 |
| Positive Control | $1.7 \times 10^8$ | $1.7 \times 10^8$ | $1.7 \times 10^8$ |

EXAMPLE 3

Effect of Gas Concentration on Decontamination Efficacy

This example demonstrates that following a pre-humidification step at 95% relative humidity and 95° F. for 1.5 hours, a concentration of 1,000 parts per million (ppm) chlorine dioxide gas is an effective sterilant for both conventional biological indicator spores and weaponized spores.

Paper filters contaminated with $2.0 \times 10^8$ weaponized spores, $10^{10}$ weaponized spores, or $10^6$ conventional biological indicator spores were enclosed in envelopes and pre-humidified at 95% relative humidity and 95° F. for 1.5 hours. They were then exposed to 2,500, 1,000, or 500 ppm $ClO_2$ for four hours. Filters were cultured under permissive culture conditions (15 hour incubation in tryptic soy broth) to determine whether the spores were viable following the decontamination protocol. Only the filters containing weaponized spores that were exposed to the lowest concentration of chlorine dioxide (500 ppm) showed viable spores following decontamination (Table 2.)

TABLE 2

Effect of gas concentration on decontamination efficacy

| | $ClO_2$ Concentration | | |
|---|---|---|---|
| | 2500 ppm | 1000 ppm | 500 ppm |
| $2 \times 10^8$ Weaponized Spores/filter | 0/2 | 0/2 | 2/2; $1.43 \times 10^3$ |
| $10^{10}$ Weaponized Spores/filter | 0/2 | 0/2 | 2/2 |
| $10^6$ Conventional Biological Indicator Spores/filter | 0/2 | 0/2 | 0/2 |
| $10^6$ Weaponized Spores/filter | | | 3/4 |
| Positive Control | $1.7 \times 10^8$ | $1.7 \times 10^8$ | $1.7 \times 10^8$ |

Thus, following a pre-humidification step at 95% relative humidity and 95° F. for 1.5 hours, a concentration of 1,000 parts per million (ppm) chlorine dioxide gas is an effective sterilant for both conventional biological indicator spores and weaponized spores.

EXAMPLE 4

Comparison of Biological Indicators at 500 PPM $ClO_2$

This example demonstrates the inadequacy of using non-weaponized spores to measure the decontamination efficiency of chlorine dioxide bioweapon decontamination protocols.

Paper filters contaminated with $10^6$ weaponized spores or $10^6$ conventional biological indicator spores were enclosed in envelopes and pre-humidified at 95% relative humidity and 95° F. for 1-3 hours. They were then exposed to 500 ppm $ClO_2$ for four hours. Filters were cultured under permissive culture conditions (15 hour incubation in tryptic soy broth) to determine whether the spores were viable following the decontamination protocol. Following decontamination, the weaponized spores were still viable, whereas the conventional biological indicator spores were not (Table 3.)

TABLE 3

Comparison of biological indicators at 500 ppm $ClO_2$

| | Humidification Time | | |
|---|---|---|---|
| | 1 hour | 2 hours | 3 hours |
| $10^6$ Weaponized Spores Per Filter | Positive | Positive | Positive |
| $10^6$ Conventional Biological Indicator Spores Per Filter | Negative | Negative | Negative |
| $10^6$ Weaponized Spores Per Filter (positive control) | Positive | Positive | Positive |
| $10^6$ Conventional Biological Indicator Spores Per Filter (positive control) | Positive | Positive | Positive |

Thus, conventional, non-weaponized spores provide an inadequate assessment of the decontamination efficiency of chlorine dioxide bioweapon decontamination protocols.

EXAMPLE 5

Efficacy of Steam Sterilization in Decontaminating Weaponized Spores Versus Conventional Bioindicator Spores This example demonstrates the inadequacy of steam sterilization for decontamination weaponized spores.

Paper filters contaminated with $10^6$ weaponized spores or $10^6$ conventional biological indicator spores were enclosed in envelopes and exposed to a steam decontamination protocol for 15 minutes at 121° C. and a pressure of 20 pounds per square inch. Filters were cultured under permissive culture conditions (15 hour incubation in tryptic soy broth) to determine whether the spores were viable following the decontamination protocol. Following decontamination, the weaponized spores were still viable, showing heavy growth with pellicle formation, whereas the conventional biological indicator spores showed no growth.

Thus, steam sterilization was ineffective at decontaminating weaponized spores.

EXAMPLE 6

Effect of Deep Vacuum and Successive Treatment Cycles on Decontamination Efficacy This example shows the effect of exposure to a deep vacuum and consecutive treatment cycles on decontamination efficacy.

Weaponized spores or conventional bioindicator spores at a concentration of $10^{10}$ were exposed to a three hour humidification step carried out at a relative humidity of 90%. Spores were then subjected to a deep vacuum of at least 29 inches of water, then were exposed to 1,000 ppm chlorine dioxide gas for four hours. In some cases, the spores were subjected to multiple treatment cycles. Spores were then cultured in tryptic soy broth to determine whether they were viable following the decontamination protocol. Table 4 shows the effects of successive $ClO_2$ treatment cycles on decontamination efficacy.

TABLE 4

Consecutive Chlorine Dioxide Treatments

| Indicator | Cycle 1 | Cycle 2 | Cycle 3 |
|---|---|---|---|
| $10^{10}$ Weaponized Spores | $5.7 \times 10^4$ | 0 | $3.3 \times 10^1$ |
| TP 10 | $4.3 \times 10^5$ | $1.3 \times 10^3$ | $7.2 \times 10^2$ |
| $10^{10}$ Weaponized Spores + Control | $1.8 \times 10^{10}$ | $1.8 \times 10^{10}$ | $1.8 \times 10^{10}$ |
| TP 10 + Control | $1.9 \times 10^{10}$ | $1.9 \times 10^{10}$ | $1.9 \times 10^{10}$ |

Thus, exposing spore-contaminated articles to a deep vacuum prior to application of chlorine over multiple cycles can increase decontamination efficacy.

EXAMPLE 7

Effect of Exposure Time and Chlorine Dioxide Concentration on Decontamination

This example shows that increasing the exposure time to chlorine dioxide gas increases decontamination efficacy, that longer exposure times are required for spores contained in an envelope than for free spores, and that longer exposure times are required for weaponized spores than for non-weaponized spores.

Weaponized spores or conventional bioindicator spores (MS) at a concentration of $10^{10}$ were either prepared as free spores or confined to glassine envelopes. Spores were then exposed to a three hour humidification step carried out at a relative humidity of 90%, and were then subjected to a deep vacuum of at least 29 inches of water. Spores were then exposed to 1,000 ppm chlorine dioxide gas for 0.5 to 6 hours (Tables 5-16). Spores were then plated in serial dilutions on agar plates and the resulting colonies were counted to determine decontamination efficacy. In addition, spores were cultured in tryptic soy broth for 24-48 hours to determine whether they were viable following the decontamination protocol.

Figure 5:
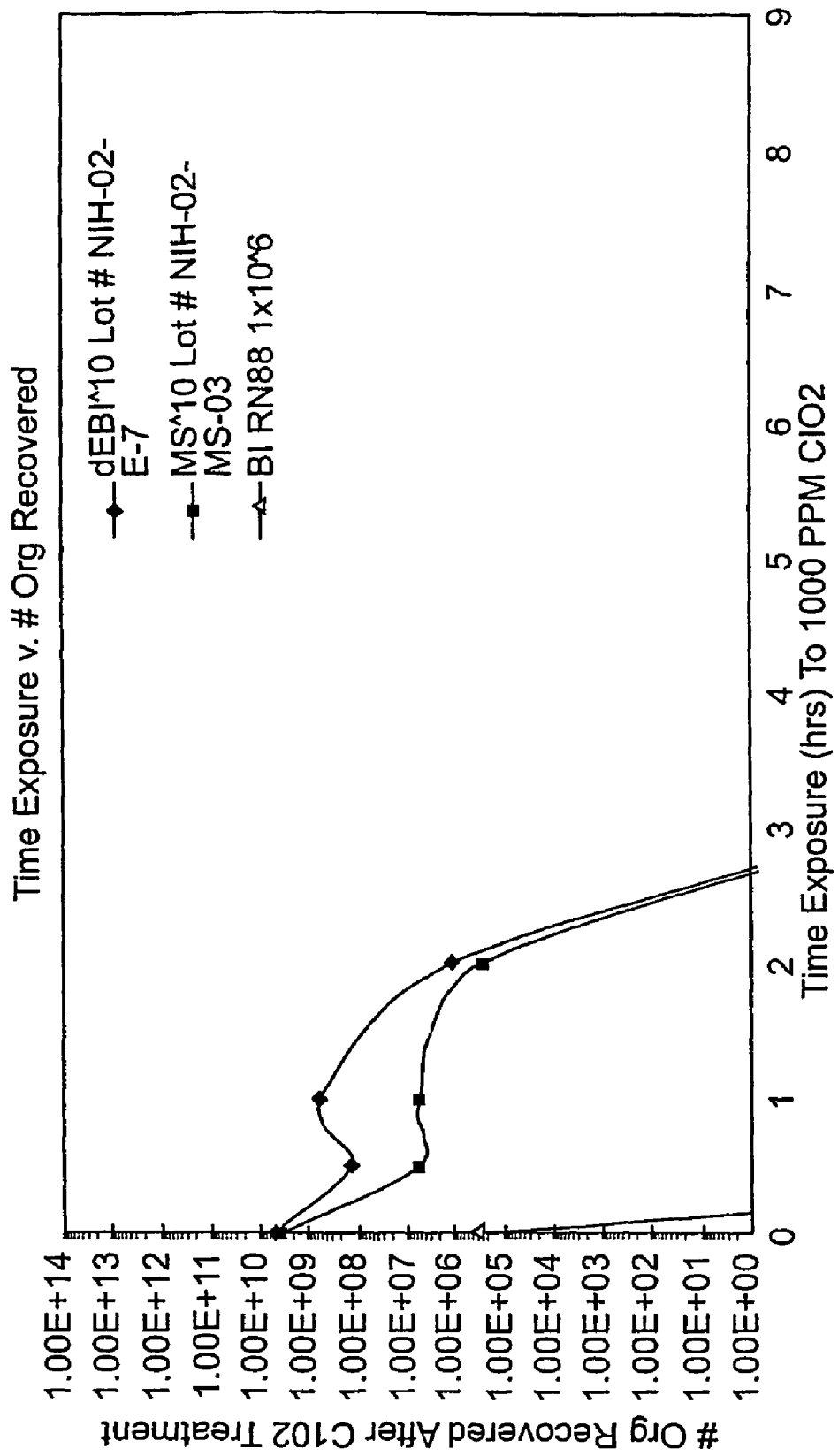
FIG. 5 is a graph showing the number of organisms recovered after exposure to 1,000 ppm ClO$_2$ following exposure to a deep vacuum.

Tables 5-16 show the effects of chlorine dioxide exposure time on decontamination of free spores versus spores in envelopes, and the differences in decontamination efficacy on weaponized spores versus conventional bioindicator spores. The results shown in Tables 5-16 are summarized in FIG. 5.

TABLE 5

Decontamination efficacy of 0.5 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 0 | 0 | 0 | − | − |
| $MS^{10}$ 5 | 0 | 0 | 0 | − | − |
| $10^{10}$ Weaponized Spores 1 | 870 | 87 | 0 | + | + |
| $10^{10}$ Weaponized Spores 2 | 410 | 57 | 3 | + | + |
| $10^{10}$ Weaponized Spores 3 | 1090 | 97 | 10 | + | + |
| $10^{10}$ Weaponized Spores 4 | 533 | 27 | 0 | + | + |
| $10^{10}$ Weaponized Spores 5 | 1527 | 13 | 3 | + | + |
| PBS - Control | 0 | 0 | 0 | − | − |

TABLE 6

Decontamination efficacy of 0.5 hour incubation of spores in glassine envelopes

| Envelope | $10^{-2}$ (Dilution on agar) | $10^{-3}$ (Dilution on agar) | $10^{-4}$ (Dilution on agar) | Broth 24 Hrs. | Broth 48 Hrs. |
|---|---|---|---|---|---|
| $MS^{10}$ 1 | TNTC | TNTC | TNTC | + | + |
| $MS^{10}$ 2 | TNTC | TNTC | 1460 | + | + |
| $MS^{10}$ 3 | 0 | 0 | 0 | + | + |
| $MS^{10}$ 4 | TNTC | TNTC | TNTC | + | + |

| Envelope | $10^{-6}$ (Dilution on agar) | $10^{-7}$ (Dilution on agar) | $10^{-8}$ (Dilution on agar) | | |
|---|---|---|---|---|---|
| $10^{10}$ Weaponized Spores 1 | TNTC | 3427 | 40 | + | + |
| $10^{10}$ Weaponized Spores 2 | TNTC | TNTC | 960 | + | + |
| $10^{10}$ Weaponized Spores 3 | TNTC | 2023 | 180 | + | + |
| $10^{10}$ Weaponized Spores 4 | TNTC | TNTC | 687 | + | +− |
| PBS - Control | 0 | 0 | 0 | − | − |

TABLE 7

Decontamination efficacy of 1 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 3 | 0 | 0 | + | + |
| $MS^{10}$ 5 | 0 | 0 | 0 | − | − |
| $10^{10}$ Weaponized Spores 1 | 0 | 0 | 0 | − | − |
| $10^{10}$ Weaponized Spores 2 | 1873 | 103 | 30 | + | + |
| $10^{10}$ Weaponized Spores 3 | 0 | 13 | 0 | + | + |
| $10^{10}$ Weaponized Spores 4 | 7 | 3 | 3 | + | + |
| $10^{10}$ Weaponized Spores 5 | 3 | 0 | 0 | + | + |
| PBS - Control | 0 | 0 | 0 | − | − |

TABLE 8

Decontamination efficacy of 1 hour incubation of spores in glassine envelopes

| Envelope | $10^{-2}$ (Dilution on agar) | $10^{-3}$ (Dilution on agar) | $10^{-4}$ (Dilution on agar) | Broth 24 Hrs. | Broth 48 Hrs. |
|---|---|---|---|---|---|
| $MS^{10}$ 1 | 0 | ND | ND | + | + |
| $MS^{10}$ 2 | 0 | ND | ND | + | + |
| $MS^{10}$ 3 | 0 | ND | ND | + | + |
| $MS^{10}$ 4 | 2100 | ND | ND | + | + |

| | $10^{-4}$ (Dilution on agar) | $10^{-5}$ (Dilution on agar) | $10^{-6}$ (Dilution on agar) | | |
|---|---|---|---|---|---|
| $10^{10}$ Weaponized Spores 1 | TNTC | 3427 | 40 | + | + |
| $10^{10}$ Weaponized Spores 2 | TNTC | TNTC | 960 | + | + |
| $10^{10}$ Weaponized Spores 3 | TNTC | 2023 | 180 | + | + |
| $10^{10}$ Weaponized Spores 4 | TNTC | TNTC | 687 | + | +− |
| PBS - Control | 0 | 0 | 0 | − | − |

TABLE 9

Decontamination efficacy of 2 hour incubation of spores in glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | TNTC | TNTC | TNTC | + | + |
| $MS^{10}$ 2 | 0 | 0 | 0 | + | + |
| $MS^{10}$ 3 | 0 | 0 | 0 | + | + |
| $MS^{10}$ 4 | 0 | 0 | 0 | + | + |
| $10^{10}$ Weaponized Spores 1 | 0 | 0 | 0 | + | + |
| $10^{10}$ Weaponized Spores 2 | TNTC | TNTC | 4350 | + | + |
| $10^{10}$ Weaponized Spores 3 | 3203 | 463 | 53 | + | + |
| $10^{10}$ Weaponized Spores 4 | 0 | 0 | 0 | + | + |
| PBS - Control | 0 | 0 | 0 | − | − |

TABLE 10

Decontamination efficacy of 2 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | + | + |
| $MS^{10}$ 4 | 0 | 0 | 0 | − | − |
| $MS^{10}$ 5 | 0 | 0 | 0 | − | − |
| $10^{10}$ Weaponized Spores 1 | 0 | 0 | 0 | − | − |
| $10^{10}$ Weaponized Spores 2 | 0 | 0 | 0 | − | − |
| $10^{10}$ Weaponized Spores 3 | 0 | 0 | 0 | − | + |
| $10^{10}$ Weaponized Spores 4 | 0 | 0 | 0 | − | − |
| $10^{10}$ Weaponized Spores 5 | 0 | 0 | 0 | − | − |
| PBS - Control | 0 | 0 | 0 | − | − |

TABLE 11

Decontamination efficacy of 3 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 0 | 0 | 0 | − | − |
| $MS^{10}$ 5 | 0 | 0 | 0 | − | − |
| $10^{10}$ Weaponized Spores 1 | 0 | 0 | 0 | − | − |

TABLE 11-continued

Decontamination efficacy of 3 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| Weaponized Spores 2 $10^{10}$ | 0 | 0 | 0 | − | − |
| Weaponized Spores 3 $10^{10}$ | 0 | 0 | 0 | − | − |
| Weaponized Spores 4 $10^{10}$ | 0 | 0 | 0 | − | − |
| Weaponized Spores 5 PBS - Control | 0 | 0 | 0 | − | − |

TABLE 12

Decontamination efficacy of 4 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 0 | 0 | 0 | − | − |
| $MS^{10}$ 5 | 0 | 0 | 0 | − | − |
| $10^{10}$ | 0 | 0 | 0 | − | − |
| Weaponized Spores 1 $10^{10}$ | 0 | 0 | 0 | − | − |
| Weaponized Spores 2 $10^{10}$ | 0 | 0 | 0 | − | − |
| Weaponized Spores 3 $10^{10}$ | 0 | 0 | 0 | − | − |
| Weaponized Spores 4 $10^{10}$ | 0 | 0 | 0 | − | − |
| Weaponized Spores 5 PBS - Control | 0 | 0 | 0 | − | − |

TABLE 13

Decontamination efficacy of 4 hour incubation of spores in glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | + | + |
| $MS^{10}$ 2 | 0 | 0 | 0 | + | + |
| $MS^{10}$ 3 | 0 | 0 | 0 | + | + |
| $MS^{10}$ 4 | 0 | 0 | 0 | + | + |
| $10^{10}$ | 0 | 0 | 0 | + | + |
| Weaponized Spores 1 $10^{10}$ | 10 | 0 | 10 | + | + |
| Weaponized Spores 2 $10^{10}$ | 0 | 0 | 0 | + | + |
| Weaponized Spores 3 $10^{10}$ | 0 | 0 | 0 | + | + |
| Weaponized Spores 4 PBS - Control | 0 | 0 | 0 | − | − |

TABLE 14

Decontamination efficacy of 5 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 0 | 0 | 0 | − | − |
| $MS^{10}$ 5 | 0 | 0 | 0 | − | − |
| $10^{10}$ | 0 | 0 | 0 | − | − |
| Weaponized Spores 1 $10^{10}$ | 0 | 0 | 0 | − | − |
| Weaponized Spores 2 $10^{10}$ | 0 | 0 | 0 | − | − |
| Weaponized Spores 3 $10^{10}$ | 0 | 0 | 0 | − | − |
| Weaponized Spores 4 $10^{10}$ | 0 | 0 | 0 | − | − |
| Weaponized Spores 5 PBS - Control | 0 | 0 | 0 | − | − |

TABLE 15

Decontamination efficacy of 6 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | − | − |
| $MS^{10}$ 2 | 0 | 0 | 0 | − | − |
| $MS^{10}$ 3 | 0 | 0 | 0 | − | − |
| $MS^{10}$ 4 | 0 | 0 | 0 | − | − |
| $MS^{10}$ 5 | 0 | 0 | 0 | − | − |
| $10^{10}$ | 0 | 0 | 0 | − | − |
| Weaponized Spores 1 $10^{10}$ | 0 | 0 | 0 | − | − |
| Weaponized Spores 2 $10^{10}$ | 0 | 0 | 0 | − | − |
| Weaponized Spores 3 $10^{10}$ | 0 | 0 | 0 | − | − |
| Weaponized Spores 4 $10^{10}$ | 0 | 0 | 0 | − | − |

TABLE 15-continued

Decontamination efficacy of 6 hour incubation of spores without glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| Weaponized Spores 5 | | | | | |
| PBS - Control | 0 | 0 | 0 | – | – |

TABLE 16

Decontamination efficacy of 6 hour incubation of spores in glassine envelopes

| Envelope | $10^{-1}$ (Dilution on agar) | $10^{-2}$ (Dilution on agar) | $10^{-3}$ (Dilution on agar) | Broth 24 Hrs. | Broth 48 Hrs. |
|---|---|---|---|---|---|
| $MS^{10}$ 1 | 0 | 0 | 0 | + | + |
| $MS^{10}$ 2 | 0 | 0 | 0 | + | + |
| $MS^{10}$ 3 | 0 | 0 | 0 | + | + |
| $MS^{10}$ 4 | 0 | 0 | 0 | + | + |
| $10^{10}$ Weaponized Spores 1 | 0 | 0 | 0 | + | + |
| $10^{10}$ Weaponized Spores 2 | 10 | 0 | 10 | + | + |
| $10^{10}$ Weaponized Spores 3 | 0 | 0 | 0 | + | + |
| $10^{10}$ Weaponized Spores 4 | 0 | 0 | 0 | + | + |
| PBS - Control | 0 | 0 | 0 | – | – |

Thus, increasing the exposure time to chlorine dioxide gas increases decontamination efficacy, longer exposure times are required for spores contained in an envelope than for free spores, and longer exposure times are required for weaponized spores than for non-weaponized spores.

This disclosure provides methods and apparatus for decontaminating articles such as a porous article. It will be apparent that the precise details of the methods and apparatus described may be varied or modified without departing from the spirit of the described disclosure. We claim all such modifications and variations that fall within the scope and spirit of the claims below.

We claim:

1. An apparatus for decontaminating an article, comprising:
   a selectively sealable decontamination chamber;
   a decontamination chamber humidifier;
   a source of chlorine dioxide gas in fluid communication with the decontamination chamber;
   a decontamination chamber vacuum generator
   a first fluid flow path for transferring humidified gas from the decontamination chamber humidifier to the selectively sealable decontamination chamber;
   a second fluid flow path for transferring chlorine dioxide gas from the source of chlorine dioxide to the selectively sealable decontamination chamber; and
   a third fluid flow path for evacuating the selectively sealable decontamination chamber via the decontamination chamber vacuum generator.

2. The apparatus of claim 1, further comprising a flow regulator in the first fluid flow path.

3. The apparatus of claim 1, further comprising a rotameter in the first fluid flow path.

4. The apparatus of claim 1, further comprising a nitrogen source and a fourth fluid flow path for transferring nitrogen gas to the decontamination chamber humidifier.

5. The apparatus of claims 4, further comprising a fill valve in the fourth fluid flow path.

6. The apparatus of claim 4, further comprising a flow regulator in the fourth fluid flow path.

7. The apparatus of claim 1, further comprising a flow regulator in the third fluid flow path.

8. The apparatus of claim 1, further comprising a ventilation valve in the second fluid flow path.

9. The apparatus of claim 1, wherein the source of chlorine dioxide gas is a chlorine dioxide generator.

10. The apparatus of claim 1, wherein the selectively sealable decontamination chamber is a rigid container.

11. The apparatus of claim 1, wherein the apparatus further comprises a heat source for providing heat to the selectively sealable decontamination chamber.

12. The apparatus of claim 1, wherein the apparatus further comprises a hygrometer for regulating humidity in the selectively sealable decontamination chamber.

13. The apparatus of claim 10, wherein the rigid container comprises a heat source, a thermostat for regulating the heat source, and a hygrometer for regulating humidity in the rigid container.

14. The apparatus of claim 1, wherein the selectively sealable decontamination chamber comprises an autoclave or a hypobaric chamber.

15. An apparatus for decontaminating a room or building, comprising:
   a decontamination chamber humidifier;
   a source of chlorine dioxide gas in fluid communication with the room or building, wherein the room or building is selectively sealable;
   a decontamination chamber vacuum generator;
   a first fluid flow path for transferring humidified gas from the decontamination chamber humidifier to the room or building;
   a second fluid flow path for transferring chlorine dioxide gas from the source of chlorine dioxide to the room or building; and
   a third fluid flow path for evacuating the room or building via the decontamination chamber vacuum generator.

16. The apparatus of claim 15, wherein the source of chlorine dioxide gas is a chlorine dioxide generator.

17. The apparatus of claim 1, wherein the selectively sealable decontamination chamber comprises a room or a building.

18. The apparatus of claim 1, wherein the article is contaminated with weaponized spore.

19. The apparatus of claim 18, wherein the weaponized spore comprises a *Bacillus anthracis* spore.

20. The apparatus of claim 1, wherein the article comprises a porous article.

21. The apparatus of claim 20, wherein the porous article comprises paper.

22. The apparatus of claim 1, wherein the article comprises a non-porous article.

23. The apparatus of claim 22, wherein the non-porous article comprises metal or glass.

24. The apparatus of claim 15, further comprising a flow regulator in the first fluid flow path.

25. The apparatus of claim 15, further comprising a rotameter in the first fluid flow path.

26. The apparatus of claim 15, further comprising a nitrogen source and a fourth fluid flow path for transferring nitrogen gas to the room or building.

27. The apparatus of claim 26, further comprising a fill valve in the fourth fluid flow path.

28. The apparatus of claim 26, further comprising a flow regulator in the fourth fluid flow path.

29. The apparatus of claim 15, further comprising a flow regulator in the third fluid flow path.

30. The apparatus of claim 15, further comprising a ventilation valve in the second fluid flow path.

31. The apparatus of claim 15, wherein the apparatus further comprises a heat source for providing heat to the room or building.

32. The apparatus of claim 15, wherein the apparatus further comprises a hygrometer for regulating humidity in the room or building.

33. The apparatus of claim 15, wherein the room or building comprises a heat source, a thermostat for regulating the heat source, and a hygrometer for regulating humidity in the room or building.

* * * * *